United States Patent [19]

Goldstein et al.

[11] 4,219,644

[45] Aug. 26, 1980

[54] FORTIMICINS AH AND AI

[75] Inventors: Alma W. Goldstein, Lake Bluff; Earl E. C. Fager, Lake Villa, both of Ill.

[73] Assignee: Abbott Laboratories, North Chicago, Ill.

[21] Appl. No.: 25,252

[22] Filed: Mar. 29, 1979

[51] Int. Cl.$^2$ .................... A61K 31/71; C07H 15/22
[52] U.S. Cl. .................................. 536/17 R; 536/18
[58] Field of Search .......................................... 536/17

[56] References Cited

U.S. PATENT DOCUMENTS

| | | | |
|---|---|---|---|
| 3,931,400 | 1/1976 | Nara et al. | 424/118 |
| 3,976,768 | 8/1976 | Nara et al. | 536/17 |
| 4,091,032 | 5/1978 | Tadanier et al. | 536/17 |
| 4,124,756 | 11/1978 | Martin et al. | 536/17 |

*Primary Examiner*—Johnnie R. Brown
*Attorney, Agent, or Firm*—Robert L. Niblack; Gildo E. Fato; Joyce R. Niblack

[57] ABSTRACT

New fortimicins, fortimicins AH and AI. The compounds are coproduced in the fermentation of *Micromonospora olivoasterospora* ATCC No. 21819, 31009 or 31010 along with fortimicin A, Isofortimicin, Fortimicin E and a number of other minor factors. The compounds are useful as an intermediate in synthesizing fortimicins AH and AI derivatives which are useful as antibiotics.

2 Claims, No Drawings

FORTIMICINS AH AND AI

BACKGROUND OF THE INVENTION

The aminoglycoside antibiotics are a valuable therapeutic class of antibiotics which include the kanamycins, gentamycins, streptomycins, sagamicins and the more recently discovered fortimicins. While the naturally produced parent antibiotics are generally, in themselves, valuable antibiotics, chemical modifications have been found to improve the activity, either intrinsic activity or activity against resistant strains or against one or more strains the parent antibiotic is not effective against. Thus, chemical modification has provided both alternative therapeutic agents as well as those which are held in reserve because of the resistance problem. And, because of the development of aminoglycoside-resistant strains and inactivation of the parent antibiotics by R-mediated factors which can develop, the search for new therapeutic entities continues.

Further, some of the naturally produced, parent antibiotics, such as fortimicin B and fortimicin E, are primarily useful as intermediates in preparing derivatives which have more potent antibacterial properties than their weakly active parent antibiotics. The present invention provides two such fortimicins, fortimicins AH and AI.

The fortimicins of this invention are co-produced in the fermentation of *Micromonospora olivoasterospora* ATCC No. 21819,31009 or 31010 according to the method of Nara et al. U.S. Pat. Nos. 3,931,400 and 3,976,768 which disclose the production of fortimicin A and fortimicin B.

Fortimicins AH and AI are minor factors which are co-produced with fortimicin A, fortimicin B and a number of other minor factors which are the subject of copending commonly assigned patent application Ser. Nos. 025,241; 025,243; 025,247; 025,250; and 025,251, filed of even date herewith and with the minor factors disclosed and claimed in commonly assigned, copending United States patent application Ser. Nos. 863,015 and 863,016, both filed Dec. 21, 1977.

SUMMARY OF THE INVENTION

The present invention provides new fortimicins, fortimicins AH and AI. The fortimicins of this invention are useful as intermediates in preparing fortimicin AH and AI derivatives which are useful as antibiotics against susceptible gram positive and gram negative bacilli such as *Escherichia coli, Staphylococcus aureus, Pseudomonas aeruginosa, Bacillis subtilis, Proteus vulgaris, Shigella sonnei, Salmonella typhi* and *Klebsiella pneumonia*.

DETAILED DESCRIPTION OF PREFERRED EMBODIMENTS

The compounds of this invention, fortimicin AH and AI are represented by the Formulae I and II respectively.

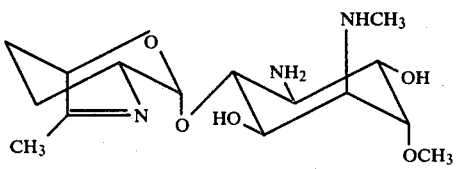

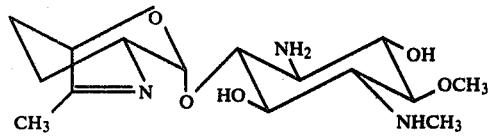

Fortimicins AH and AI are useful as intermediates in the preparation of the 4-N-fortimicin AH and AI derivatives set forth in Formulae III and IV and disclosed and claimed in commonly assigned, copending application Ser. No. 025,254, filed of even date.

Illustrative of fortimicin AH and AI derivatives which can be prepared from the compound of this invention are derivatives represented by Formulae III and IV respectively.

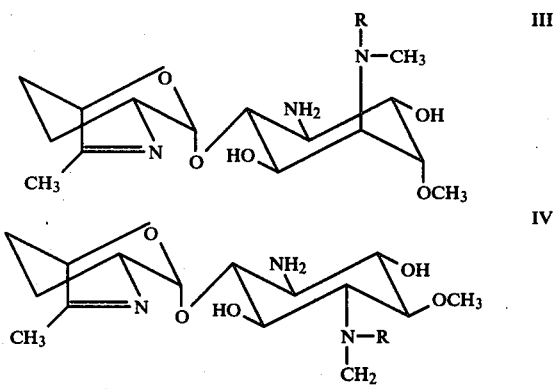

wherein R is hydrogen, acyl, aminoacyl, diaminoacyl, N-loweralkylaminoacyl, N,N-diloweralkylaminoacyl, hydroxysubstituted aminoacyl, loweralkyl, aminoloweralkyl, diaminoloweralkyl, hydroxyloweralkyl, N-loweralkylaminoloweralkyl, aminohydroxyloweralkyl, N,N-diloweralkylaminoloweralkyl, N-loweralkylaminohydroxyloweralkyl, or N,N-diloweralkylaminohydroxyloweralkyl and the pharmaceutically acceptable salts thereof.

The term "acyl", as used in the above definitions refers to acyl radicals of loweralkylcarboxylic acids represented by the formula

wherein R is loweralkyl, i.e., acetyl, propionyl, butyryl, valeryl, etc.

The terms aminoacyl, hydroxy-substituted aminoacyl, etc., enumerated in the definition of R in Formulae III and IV include, but are not limited to as will be obvious to those skilled in the art, naturally occuring amino acids such as glycyl, valyl, alanyl, sarcosyl, leucyl, isoleucyl, prolyl, seryl, and like amino acid residues as well as groups such as 2-hydroxy-4-aminobutyryl and like groups. The amino acid residues included in the above terms, with the exception of glycyl, can be either in the L- or D-configurations or mixtures thereof.

The term "loweralkyl", as used herein, refers to straight or branched chain alkyl radicals containing from 1 to 6 carbon atoms and includes, but is not limited to, methyl, ethyl, n-propyl, iso-propyl, n-butyl, isobutyl, tert-butyl, n-pentyl, 1-methylbutyl, 2,2-dimethylpropyl, n-hexyl, 2-methylpentyl and the like radicals.

The term "pharmaceutically acceptable salts" refers to the non-toxic acid addition salts of the compounds of Formulae III and IV which can be prepared either in situ during the final isolation and purification or by separately reacting the free base with a suitable organic or inorganic acid by methods well known in the art. Representative salts include the mono-, di-, tri-tetra, or other per-salts such as the hydrochloride, hydrobromide, sulfate, bisulfate, acetate, oxalate, valerate, oleate, palmitate, stearate, laurate, borate, benzoate, lactate, phosphate, tosylate, citrate, maleate, fumarate, succinate, tartrate, napsylate and like salts.

The antibiotics of Formulae III and IV are effective antibacterial agents against susceptible or sensitive strains of gram-negative and gram-positive bacili such as *Staphylococcus aureus, Escherichia coli, Pseudomonas aeruginosa, Bacillus subtilis, Proteus vulgaris, Shigella sonnei, Salmonella typhi* and *Klebsiella pneumoniae*. The compounds of Formula II are administered parenterally, i.e., intravenously, intramuscularly, intraperitoneally, or subcutaneously for systemic effect in daily dosages of from 20 to 40 mg/kg of body weight daily, preferrably from 25 to 30 mg/kg of body weight daily based on lean body weight as is good medical practice with the aminoglycoside antibiotics and are preferrably administered in divided dosages. The compounds can also be administered orally at the above dosages to sterilize the intestinal tract and can further be administered in suppository form.

The term "sensitive or susceptible strains" refers to strains of bacilli or organisms which have been demonstrated to be sensitive to a particular antibiotic in a standard in vitro sensitivity test and thus in vitro activity has been established for a particular antibiotic against a specific strain of a specific organism.

Fortimicin AH and AI can be prepared by the fermentation of *Micromonospora olivoasterospora* ATCC No. 21819,31009 or 31010 according to the methods described by Nara et al. in U.S. Pat. Nos. 3,931,400 and 3,976,768 for the fermentation of fortimicin A and fortimicin B, and set forth in Examples 1-4 for the fermentation and isolation of fortimicins AH and AI.

The 4-N-acyl fortimicin AI derivatives are prepared following the general procedure used for the preparation of 4-N-acyl derivatives of fortimicins having the fortimicin E stereochemistry for the 4-N-position as disclosed in commonly assigned, co-pending U.S. application Ser. No. 863,010, filed Dec. 21, 1977.

Generally speaking, the 4-N-acyl derivatives can be prepared by reacting 1 mole of salicylaldehyde with fortimicin which results in the formation of 1-N-salicylaldehyde Schiff base fortimicin AI. The latter can then be aminoacylated by coupling the Schiff base intermediate with a variety of activated carboxylic acid derivatives such as a carboxylic acid anhydride, a carboxylic acid chloride, an active carboxylic acid ester or a carboxylic acid azide.

The active esters may be conveniently prepared by reacting the appropriate carboxylic acid, RCOOH with, for example 1-hydroxybenzotriazole, N-hydroxysuccinimide or N-hydroxy-5-norbornene-2,3-dicarboximide according to the method of M. Fujino et al., *Chem Pharm Bull,* Japan 22:1857 (1974) wherein R is as defined in formula II for acyl and acyl-containing groups.

For example, the Schiff base fortimicin AI can be aminoacylated with an active ester represented by the formula A-R-Z i.e., N-benzyloxycarbonylglycyl-N-hydroxysuccinimide active ester (A=ONS, R=COCH$_2$NH—), N-benzyloxycarbonyl-$\beta$-alanyl-N-hydroxy-5-norbornene-2,3-dicarboximide active ester (A=ONB, R=COCH$_2$CH$_2$NH-), N-benzyloxycarbonylsarcosyl-N-hydroxy-5-norbornene-2,3-dicarboximide active ester (A=ONB), R=COCH$_2$N(CH$_3$—)—), and N-benzyloxycarbonyl-L-(2-hydroxy-4-amino)butyryl-N-hydroxy-5-norbornene-2,3-dicarboximide active ester (A=ONB, R=COCH(OH)CH$_2$CH$_2$NH—) where the symbol Z refers to the benzyloxycarbonyl group

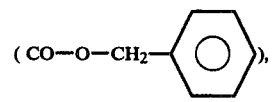

ONB refers to N-hydroxynorbornyldicarboximide and ONS refers to N-(benzyloxycarbonyloxy)succinimide.

After the above illustrative couplings, the following intermediates are obtained:4-N-(N-benzyloxycarbonylglycyl)-1-N-salicylaldehyde Schiff base fortimicin AI; 4-N-(N-benzyloxycarbonyl-beta-alanyl)-1-N-salicylaldehyde Schiff base fortimicin AI; 4-N-(N-benzyloxycarbonylsarcosyl)-1-N-salicylaldehyde Schiff base fortimicin AI; and 4-N-[N-benzyloxycarbonyl-(L-2-hydroxy-4-aminobutyryl)]-1-N-salicylaldehyde Schiff base fortimicin AI respectively.

It will be readily apparent to those skilled in the art that by substituting the appropriate R group, any of the acyl-containing intermediates for the corresponding final products can be obtained.

The Schiff base intermediates are treated with 0.2 N aqueous hydrochloric acid to cleave the Schiff base protecting groups and the resulting crude hydrochloride salts are subjected to silica gel chromatography in a solvent system containing ammonium hydroxide which results in the following illustrative, partially deprotected intermediates:4-N-(N-benzyloxycarbonylglycyl)fortimicin AI; 4-N-(N-benzyloxycarbonyl-beta-alanyl)fortimicin AI; 4-N-(N-benzyloxycarbonylsarcosyl)fortimicin AI; and 4-N-[N-benzyloxycarbonyl-(L-2-hydroxy-4-aminobutyryl)]-fortimicin AI. The 4-N-protected intermediates are then reacted with N-benzyloxycarbonyloxy-5-norbornene-2,3-dicarboximide (Z-ONB) to form the corresponding di-N-protected intermediates, i.e. di-N-benzyloxycarbonyl-4-N-glycylfortimicin AI.

Hydrogenolysis of the di-N-protected intermediates over palladium on carbon catalyst (5% Pd/C) in, for example 0.2 N hydrochloric acid in methanol yields the desired final products, i.e. 4-N-glycylfortimicin AI dihydrochloride, 4-N-sarcosylfortimicin AI dihydrochloride, etc.

4-N-alkylation is readily accomplished by reducing the corresponding acyl, hydroxyacyl or amino-containing acyl product with diborane.

4-N-acylation of fortimicin AH is accomplished by the method disclosed in U.S. Pat. No. 4,091,032 which discloses 4-N-fortimicin B derivatives.

It is understood that the terms acyl and alkyl have, for the purpose of the above discussion have been used as shorthand references to the terms "loweralkyl" and "acyl" defined on pages 3 and 4 of the specification and to the acyl and alkyl-containing definitions for R and R$_1$ is Formula II. This shorthand reference has been used to simplify the above discussion, not to modify the terms as defined.

The following Examples further illustrate the present invention by setting forth the fermentation and isolation of fortimicins AH and AI which are coproduced with fortimicin A, fortimicin B, isofortimicin, fortimicin E and a number of other minor factors.

Fortimicins AH and AI can be prepared by the fermentation of *Micromonospora olivoasterospora* ATCC 21819 in a suitable fermentation broth and isolated as described hereinbelow.

EXAMPLE 1

Preparation of Fermentation Broth

6000 Liters of a fermentation broth having the following composition and pH 7 before sterilization is prepared:

| Ingredient | Weight Percent |
| --- | --- |
| Starch | 4.00 |
| Soybean meal | 2.00 |
| Cornsteep liquor | 0.05 |
| $K_2HPO_4$ | 0.05 |
| $MgSO_4 \cdot 7 H_2O$ | 0.05 |
| KCl | 0.03 |
| $CaCO_3$ | 0.1 |
| Water | to 100.00 |

EXAMPLE 2

Preparation of Inoculum

*Micromonospora olivoasterospora* ATCC 21819 is used as a seed strain and is initially cultured in a first seed medium containing 2% glucose, 0.5% peptone, 0.5% yeast extract and 0.1% calcium carbonate (pH 7.2 before sterilization) by inoculating one loopful of the seed strain into 10 ml of the seed medium in a 50 ml large test tube. Culturing is carried out at 30° C. for 5 days with shaking. Ten ml of the seed culture broth is then inoculated into 30 ml of a second seed medium in a 250 ml Erlenmeyer flask. The composition of the second seed medium is the same as that of the first seed medium. The second seed culturing is carried out at 30° C. for two days with shaking.

Then 30 ml of the second seed culture broth is inoculated into 300 ml of a third seed medium in a two liter Erlenmeyer flask provided with baffles. The composition of the third seed medium is the same as that of the first seed medium and the third seed culturing is carried out at 30° C. for 2 days with shaking. Thereafter, 1.5 liters of the third seed culture broth (corresponding to the contents of five flasks) is inoculated into 5 liters of a fourth seed medium in a 30 liter glass jar fermenter. The composition of the fourth seed medium is the same as that of the first seed medium. Culturing in the jar fermenter is carried out at 30° C. for two days with aeration (15 liters/min) and stirring (350 r.p.m.).

EXAMPLE 3

Production of Fortimicins AH and AI

Fifteen liters of the fourth seed culture broth of Example 2 is inoculated into 150 liters of a main fermentation medium in a 300 liter stainless steel fermenter. The main fermentation medium comprises: 4% starch, 2% soybean meal, 1% corn steep liquor, 0.05% $K_2HPO_4$, 0.05% $MgSO_4.7H_2O$, 0.3% KCL and 0.1% $CaCO_3$ and water. (pH 7.0 before sterilization) Culturing in the fermenter is carried out at 30° C. for 4 days with aeration (80 liters/min) and stirring (150 r.p.m.).

EXAMPLE 4

Isolation of Fortimicins AH and AI

To 5000 liters of the fermentation broth, prepared as described above, is added 102 liters of a weakly acidic carboxylic (polymethacrylate) type cation exchange resin in the ammonia form, e.g. Amberlite IRC-50 sold by the Rohm and Haas Company. The mixture is agitated for two hours, during which time the mixture is maintained at pH 6.6 by the addition of sulfuric acid. The ion exchange resin is separated from the broth by centrifugation and then added to a column and backwashed with deionized water until free of extraneous solids. The column is washed with water, then eluted downflow with 1 N ammonium hydroxide. Elutes of pH 9.6 to about 11.3 are collected and concentrated under reduced pressure until excess ammonia is removed. The solution is adjusted to pH 2.0 with hydrochloric acid and treated with 5%(w/v) activated carbon such as Pittsburg RB carbon sold by Calgon Corporation. The solution is then filtered through a diatomaceous earth mat and the filtrant concentrated under reduced pressure to give a mixture of crude fortimicins in methanol (5 liters).

A portion of the crude fortimicins in methanol (5 liters) is chromatographed on a column of silica gel (4 kg) eluted with methanol with an increasing gradient concentration of hydrochloric acid. Initial fractions are combined, adjusted to pH 5 and concentrated to yield 237 g (dry weight) of crude fortimicin components. A portion (40 g of the crude component mixture is dissolved in water and applied to a Bio Rad AG 2X8 resin-($OH^-$) form column and eluted with water. The fractions giving positive ninhydrin spots on thin layer chromatography (tlc) plates are combined and concentrated to give 17 g of solids. These are dissolved in water and chromatographed on a column (3.5 cm diam. ×47 cm) of Bio Rex 70 resin ($NH_4^+$ form) developed with a gradient from water (one liter) to 1 N ammonium hydroxide (1 liter). Initial fractions are combined and concentrated to yield 5.4 g of solids which are rechromatographed in two portions over a similar column of Bio RNx 70 resin($NH_4^+$ form). Fractions containing the desired components are pooled to give two concentrates containing fortimicin AH(earlier fractions) and AI (later fractons).

EXAMPLE 5

Purification of Fortimicin AH

Crude fortimicin AH(260 mg) is purified by chromatography on a column (1.5 cm diameter×61 cm) of E. Merck silica gel 60 developed with the lower phase of a mixture of chloroform, methanol, ammonium hydroxide[1.5:1:1 (v/v/v)]. Fractions containing pure fortimicin AH as detected on tlc plates are combined and concentrated to yield pure fortimicin AH(45.8 mg). PMR spectrum in deuterium oxide with external tetramethylsilane as reference: $\delta 2.65$(3H) singlet $CH_3—C_7$; $\delta$ 2.84 (3H) singlet $NCH_3$; $\delta$ 3.90 (3H) singlet $OCH_3$; $\delta$ 5.71 (1 H) doublet $C_{1'}$—H.

EXAMPLE VI

Purification of Fortimicin AI

Crude fortimicin AI (430 mg) is chromatographed on a column of E. Merck silica gel in the lower phase of a mixture of chloroform-methanol-ammonium hydroxide[1,5:1:1 (v/v/v)] and fractions containing fortimicin AI are combined and concentrated to yield 265 mg of solid which is rechromatographed on a column of silica gel developed with a mixture of chloroform-methanol-ammonium hydroxide, initially 90:10:4 (v/v/v) followed stepwise by 70:30:0.4 (v/v/v) and 70:30:0.80 (v/v/v). Fractions containing fortimicin AI are combined and concentrated to yield 60 mg which is purified by further chromatography over silica gel in chloroform-methanol-ammonium hydroxide[70:30:1.6 (v/v/v)] to give fortimicin AI(43.3 mg). Proteon magnetic resonance spectrum in deuterium oxide with tetramethylsilane as external reference:$\delta$ 2.65 (3H) singlet $C_{7'}$—$CH_3$, $\delta$ 2.89 (3H) singlet $NCH_3$, $\delta$ 4.03 (3H singlet $OCH_3$; $\delta$ 5.75 (1H) doublet $C_{1'}$—H.

We claim:

1. Fortimicin AH represented by the formula:

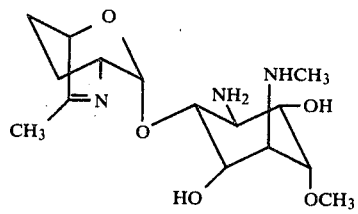

or a pharmaceutically acceptable salt thereof.

2. Fortimicin AI represented by the formula:

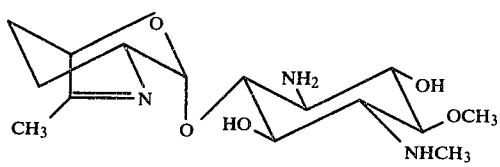

and the pharmaceutically acceptable salts thereof.

* * * * *